United States Patent
Imran

(10) Patent No.: US 8,759,284 B2
(45) Date of Patent: Jun. 24, 2014

(54) THERAPEUTIC AGENT PREPARATIONS FOR DELIVERY INTO A LUMEN OF THE INTESTINAL TRACT USING A SWALLOWABLE DRUG DELIVERY DEVICE

(75) Inventor: Mir Imran, Los Altos Hills, CA (US)

(73) Assignee: Rani Therapeutics, LLC, San Jose, CA (US)

( * ) Notice: Subject to any disclaimer, the term of this patent is extended or adjusted under 35 U.S.C. 154(b) by 207 days.

(21) Appl. No.: 12/978,164

(22) Filed: Dec. 23, 2010

(65) Prior Publication Data

US 2011/0160129 A1    Jun. 30, 2011

Related U.S. Application Data

(60) Provisional application No. 61/395,304, filed on May 10, 2010, provisional application No. 61/340,331, filed on Mar. 15, 2010, provisional application No. 61/339,941, filed on Mar. 10, 2010, provisional application No. 61/284,766, filed on Dec. 24, 2009.

(51) Int. Cl.
*A61P 3/10* (2006.01)
*A61K 9/64* (2006.01)

(52) U.S. Cl.
USPC ............... 514/6.8; 514/6.9; 424/460

(58) Field of Classification Search
None
See application file for complete search history.

(56) References Cited

U.S. PATENT DOCUMENTS

| | | |
|---|---|---|
| 3,788,322 A | 1/1974 | Micheals |
| 4,425,117 A | 1/1984 | Hugemann et al. |
| 4,596,819 A | 6/1986 | Nicolaides et al. |
| 4,663,308 A | 5/1987 | Saffran et al. |
| 4,781,685 A | 11/1988 | Lehmann et al. |
| 5,129,915 A | 7/1992 | Cantenys |
| 5,137,669 A | 8/1992 | Leonard et al. |
| 5,217,449 A | 6/1993 | Yuda et al. |
| 5,271,945 A | 12/1993 | Yoshioka et al. |
| 5,474,785 A | 12/1995 | Wright et al. |
| 5,674,205 A | 10/1997 | Pasricha et al. |
| 5,683,435 A | 11/1997 | Truex et al. |
| 5,750,926 A | 5/1998 | Schulman et al. |
| 5,795,591 A | 8/1998 | Lee et al. |
| 5,849,327 A | 12/1998 | Berliner et al. |
| 5,904,935 A | 5/1999 | Eckenhoff et al. |
| 5,987,358 A | 11/1999 | Sosebee et al. |
| 6,645,988 B2 | 11/2003 | Phillips |
| 6,656,155 B2 | 12/2003 | Freyman |
| 6,975,906 B2 | 12/2005 | Rusin et al. |
| 7,083,578 B2 | 8/2006 | Lewkowicz et al. |
| 7,083,579 B2 | 8/2006 | Yokoi et al. |
| 7,396,265 B2 | 7/2008 | Darley et al. |
| 7,502,649 B2 | 3/2009 | Ben-Haim et al. |
| 7,569,032 B2 | 8/2009 | Naimark et al. |
| 7,785,291 B2 | 8/2010 | Marco et al. |
| 7,854,745 B2 | 12/2010 | Brister et al. |
| 8,353,863 B2 | 1/2013 | Imran |
| 2002/0198470 A1 | 12/2002 | Imran et al. |
| 2004/0093039 A1 | 5/2004 | Schumert |
| 2004/0122315 A1 | 6/2004 | Krill |
| 2004/0143221 A1 | 7/2004 | Shadduck |
| 2004/0253304 A1 | 12/2004 | Gross et al. |
| 2004/0267240 A1 | 12/2004 | Gross et al. |
| 2005/0038415 A1 | 2/2005 | Rohr et al. |
| 2005/0065463 A1 | 3/2005 | Tobinaga et al. |
| 2005/0095246 A1 | 5/2005 | Shafer |
| 2005/0183733 A1 | 8/2005 | Kawano et al. |
| 2007/0016262 A1 | 1/2007 | Gross et al. |
| 2007/0066557 A1 * | 3/2007 | Monia et al. ............... 514/44 |
| 2007/0100378 A1 | 5/2007 | Maschino |
| 2007/0123809 A1 | 5/2007 | Weiss et al. |
| 2007/0161851 A1 | 7/2007 | Takizawa et al. |
| 2007/0265598 A1 | 11/2007 | Karasik |
| 2007/0277374 A1 | 12/2007 | Suaning |
| 2007/0288033 A1 | 12/2007 | Murature et al. |
| 2008/0065181 A1 | 3/2008 | Stevenson |
| 2008/0255543 A1 | 10/2008 | Tanaka et al. |
| 2008/0275430 A1 | 11/2008 | Belsky et al. |
| 2009/0004266 A1 | 1/2009 | Sung et al. |

(Continued)

FOREIGN PATENT DOCUMENTS

CN    101511305    8/2009
WO    WO 03/068061 A1    8/2003

(Continued)

OTHER PUBLICATIONS

Tao et al, DDT, 10: 909-915, 2005.*

(Continued)

*Primary Examiner* — Gyan Chandra
(74) *Attorney, Agent, or Firm* — Wilson Sonsini Goodrich & Rosati

(57) ABSTRACT

Embodiments of the invention provide swallowable devices, preparations and methods for delivering drugs and other therapeutic agents within the GI tract. Many embodiments provide a swallowable device for delivering the agents. Particular embodiments provide a swallowable device such as a capsule for delivering drugs into the intestinal wall or other GI lumen. Embodiments also provide various drug preparations that are configured to be contained within the capsule, advanced from the capsule into the intestinal wall and degrade within the wall to release the drug to produce a therapeutic effect. The preparation can be coupled to an actuator having a first configuration where the preparation is contained in the capsule and a second configuration where the preparation is advanced out of the capsule into the intestinal wall. Embodiments of the invention are particularly useful for the delivery of drugs which are poorly absorbed, tolerated and/or degraded within the GI tract.

15 Claims, 17 Drawing Sheets

(56) References Cited

U.S. PATENT DOCUMENTS

| | | |
|---|---|---|
| 2009/0030473 A1 | 1/2009 | Khawaled et al. |
| 2009/0041849 A1 | 2/2009 | New |
| 2009/0088387 A1 | 4/2009 | Castillo et al. |
| 2009/0093617 A1 | 4/2009 | Shenoy et al. |
| 2009/0187229 A1 | 7/2009 | Lavie |
| 2009/0258519 A1 | 10/2009 | Dilmaghanian et al. |
| 2009/0306633 A1 | 12/2009 | Trovato et al. |
| 2010/0021536 A1 | 1/2010 | Gross |
| 2010/0034823 A1 | 2/2010 | Borhani et al. |
| 2010/0049120 A1 | 2/2010 | Dijksman et al. |
| 2010/0056948 A1 | 3/2010 | Hornby et al. |
| 2010/0094256 A1 | 4/2010 | Kassab et al. |
| 2010/0100117 A1 | 4/2010 | Brister et al. |
| 2011/0046053 A1 | 2/2011 | Kidron |
| 2011/0098651 A1 | 4/2011 | Falo, Jr. et al. |
| 2011/0160699 A1 | 6/2011 | Imran |
| 2011/0208270 A1 | 8/2011 | Imran et al. |
| 2012/0010590 A1 | 1/2012 | Imran |

FOREIGN PATENT DOCUMENTS

| | | |
|---|---|---|
| WO | WO 2005/105053 A2 | 11/2005 |
| WO | WO 2006/064502 A2 | 6/2006 |
| WO | WO 2007/093806 A1 | 8/2007 |

OTHER PUBLICATIONS

Whitehead et al., J. controlled Rel., 98: 37-45, 2004.*
Irons and Robinson., Bioadhesives in Drug Delivery 2003.*
Yoncheva et al., European J. of Pharmaceutical Sci 24: 411-419, 2005.*
Betancourt et al., Int. J. Nanomedicine, 1: 483-495, 2006.*
U.S. Appl. No. 13/532,589, filed Jun. 25, 2012, Imran.
U.S. Appl. No. 13/538,728, filed Jun. 29, 2012, Imran.
U.S. Appl. No. 13/538,748, filed Jun. 29, 2012, Imran.
U.S. Appl. No. 13/538,770, filed Jun. 29, 2012, Imran.
U.S. Appl. No. 13/538,783, filed Jun. 29, 2012, Imran.
U.S. Appl. No. 13/538,793, filed Jun. 29, 2012, Imran.
U.S. Appl. No. 13/538,812, filed Jun. 29, 2012, Imran.
U.S. Appl. No. 13/538,823, filed Jun. 29, 2012, Imran.
U.S. Appl. No. 13/538,841, filed Jun. 29, 2012, Imran.
U.S. Appl. No. 13/538,852, filed Jun. 29, 2012, Imran.
U.S. Appl. No. 13/538,875, filed Jun. 29, 2012, Imran.
U.S. Appl. No. 13/538,903, filed Jun. 29, 2012, Imran.
U.S. Appl. No. 13/538,912, filed Jun. 29, 2012, Imran.
U.S. Appl. No. 13/539,019, filed Jun. 29, 2012, Imran.
U.S. Appl. No. 13/539,031, filed Jun. 29, 2012, Imran.
International search report dated Sep. 5, 2012 for International Application No. PCT/US2012/045138.
International search report and written opinion dated Sep. 21, 2010 for PCT/US2010/044265.
International search report dated Sep. 23, 2011 for International Application No. PCT/US2010/062070.
International search report dated Sep. 29, 2011 for International Application No. PCT/US2010/062073.
U.S. Appl. No. 13/837,025, filed Mar. 15, 2013, Imran.
Office action dated Jun. 5, 2013 for U.S. Appl. No. 12/849,574.
International search report dated Dec. 7, 2012 for International Application No. PCT/US2012/044441.
U.S. Appl. No. 13/970,446, filed Aug. 19, 2013, Imran.
Basic Pharmacokinetics; Chapter 6. www.pharmpress.com/files/docs/php-bph-c06.pdf [online] retrieved on Oct. 25, 2013; 22 pages.
Bauer, et al. Pharmazeutische Technologie. Gustav Fischer Verlag, Germany. Jan. 1, 1997; 337-349. (in German).
European search report and opinion dated Jun. 26, 2013 for EP Application No. 10807036.8.
European search report and opinion dated Jul. 26, 2013 for EP Application No. 10840193.6.
European search report and opinion dated Oct. 24, 2013 for EP Application No. 10847622.7.
Frandsen, et al. Abrams' Clinical Drug Therapy. 2013 Lippincott Williams & Wilkins. 3 pages.
Jain. The manufacturing techniques of various drug loaded biodegradable poly(lactide-co-glycolide) (PLGA) devices. Biomaterials. 2000; 21:2475-2490.
Office action dated Jun. 20, 2013 for U.S. Appl. No. 13/538,912.
Office action dated Jul. 8, 2013 for U.S. Appl. No. 13/539,019.
Office action dated Jul. 9, 2013 for U.S. Appl. No. 13/538,852.
Office action dated Aug. 26, 2013 for U.S. Appl. No. 13/538,728.
Office action dated Aug. 27, 2013 for U.S. Appl. No. 13/538,770.
Office action dated Sep. 20, 2013 for U.S. Appl. No. 12/978,233.
Office action dated Oct. 29, 2013 for U.S. Appl. No. 13/538,823.
Office action dated Oct. 31, 2013 for U.S. Appl. No. 13/539,031.
Office action dated Nov. 6, 2013 for U.S. Appl. No. 13/970,446.
Roberts, et al. Pharmacokinetics and anaesthesia. (Continuing Education in Anaesthesia, Critical Care & Pain, 2007, vol. 7: 25-29).
U.S. Appl. No. 14/179,215, filed Feb. 12, 2014, Imran et al.
Office action dated Dec. 19, 2013 for U.S. Appl. No. 13/532,589.

* cited by examiner

Degradation

THERAPEUTIC AGENT PREPARATIONS FOR DELIVERY INTO A LUMEN OF THE INTESTINAL TRACT USING A SWALLOWABLE DRUG DELIVERY DEVICE

CROSS-REFERENCES TO RELATED APPLICATIONS

This application claims the benefit of priority to U.S. Application Ser. Nos. 61/339,941 filed Mar. 10, 2010, entitled, "Swallowable Drug Delivery Device and Methods of Delivery", 61/284,766, filed Dec. 24, 2009, entitled, "Swallowable Drug Delivery Device and Methods of Drug Delivery", 61/340,331, filed Mar. 15, 2010, entitled "Swallowable Drug Delivery Device and Methods of Delivery"; and 61/395,304, filed May 10, 2010, entitled, Swallowable Drug Delivery Device and Method of Delivery" which are fully incorporated by reference herein for all purposes.

This application is also related to U.S. application Ser. No. 12/978,301, filed Dec. 23, 2010, entitled "Swallowable Drug Delivery Device and Method of Delivery"; and Ser. No. 12/978,233, filed Dec. 23, 2010, entitled, "Swallowable Drug Delivery Device and Methods of Drug Delivery"; all of which are fully incorporated by reference herein for all purposes.

BACKGROUND OF THE INVENTION

Field of the Invention

Embodiments of the invention relate to swallowable drug delivery devices. More specifically, embodiments of the invention relate to swallowable drug delivery devices for delivering drugs to the small intestine.

While there has been an increasing development of new drugs in recent years for the treatment of a variety of diseases, many have limited application because they cannot be given orally. This is due to a number of reasons including: poor oral toleration with complications including gastric irritation and bleeding; breakdown/degradation of the drug compounds in the stomach; and poor, slow or erratic absorption of the drug. Conventional alternative drug delivery methods such as intravenous and intramuscular delivery have a number of drawbacks including pain and risk of infection from a needle stick, requirements for the use of sterile technique and the requirement and associated risks of maintaining an IV line in a patient for an extended period of time. While other drug delivery approaches have been employed such as implantable drug delivery pumps, these approaches require the semi-permanent implantation of a device and can still have many of the limitations of IV delivery. Thus, there is a need for an improved method for delivery of drugs and other therapeutic agents.

BRIEF SUMMARY OF THE INVENTION

Embodiments of the invention provide devices, systems, kits and methods for delivering drugs and other therapeutic agents to various locations in the body. Many embodiments provide a swallowable device for delivering drugs and other therapeutic agents within the Gastrointestinal (GI) tract. Particular embodiments provide a swallowable device such as a capsule for delivering drugs and other therapeutic agents into the wall of the small intestine or other GI organ wall. Embodiments of the invention are particularly useful for the delivery of drugs and other therapeutic agents which are poorly absorbed, poorly tolerated and/or degraded within the GI tract. Further, embodiments of the invention can be used to deliver drugs which were previously only capable of or preferably delivered by intravenous or other form of parenteral administration (e.g., intramuscular, etc).

In one embodiment, a therapeutic agent preparation for delivery into a lumen wall of the intestinal tract, the preparation comprises a therapeutically effective dose of at least one therapeutic agent. The preparation has a shape and material consistency to be contained in a swallowable capsule and delivered from the capsule into the lumen wall to release the dose of therapeutic agent from within the lumen wall.

In another embodiment, a therapeutic agent preparation for delivery into a lumen wall of the intestinal tract, the preparation comprises a therapeutically effective dose of at least one therapeutic agent. The preparation is configured to be contained in a swallowable capsule and operably coupled to an actuator having a first configuration and a second configuration. The preparation is contained within the capsule in the first configuration and advanced out of the capsule and into the lumen wall in the second configuration to deliver the therapeutic agent into the lumen wall.

In yet another embodiment, a method for delivering a therapeutic agent into the wall of the small intestine comprises swallowing a drug delivery device comprising a capsule, an actuator and an embodiment of the therapeutic agent preparation. The actuator responsive to a condition in the small intestine is actuated to deliver the therapeutic agent preparation into the wall of the small intestine.

In one aspect, the invention provides a swallowable device for delivering drugs or other therapeutic agent into the wall of the small or large intestine. The device comprises a capsule sized to be swallowed and pass through the intestinal tract. The capsule includes an interior volume and can be fabricated from various biocompatible polymers known in the art including various biodegradable polymers. The capsule includes at least one guide tube, one or more tissue penetrating members positioned in the at least one guide tube, a delivery member and an actuating mechanism. The tissue penetrating member will typically comprise a hollow needle or other like structure and will have a lumen and a tissue penetrating end for penetrating a selectable depth into the intestinal wall. In various embodiments, the device can include a second and a third tissue penetrating member with additional numbers contemplated. Each tissue penetrating member can include the same or a different drug. In preferred embodiments having multiple tissue penetrating members, the tissue penetrating members can be symmetrically distributed around the perimeter of the capsule so as to anchor the capsule onto the intestinal wall during delivery of drug. In some embodiments, all or a portion of the tissue penetrating member (e.g., the tissue penetrating end) can be fabricated from the drug itself. In these and related embodiments, the drug can have a needle or dart-like structure (with or without barbs) configured to penetrate and be retained in the intestinal wall.

The tissue penetrating member can be fabricated from various biodegradable materials (e.g., PGLA) so as to degrade within the small intestine and thus provide a fail-safe mechanism for detaching the tissue penetrating member from the intestinal wall should this component become retained in the intestinal wall. Additionally, in theses and related embodiments, selectable portions of the capsule can be fabricated from such biodegradable materials so as to allow the entire device to controllably degrade into smaller pieces. Such embodiments facilitate passage and excretion of the devices through GI tract. In particular embodiments, the capsule can include seams of biodegradable material which controllably degrade to produce capsule pieces of a selectable size and shape to facilitate passage through the GI tract. The seams can be pre-stressed, perforated or otherwise treated to accelerate degradation. The concept of using biodegradable seams to produce controlled degradation of a swallowable device in the GI tract can also be applied to other swallowable devices such as swallowable cameras to facilitate passage through the GI tract and reduce the likelihood of a device becoming stuck in the GI tract.

The delivery member is configured to advance the drug from the capsule through the tissue penetrating member lumen and into the intestinal wall. Typically, at least a portion of the delivery member is advanceable within the tissue penetrating member lumen. The delivery member can have a piston or like structure sized to fit within the delivery member lumen. The distal end of the delivery member (the end which is advanced into tissue) can have a plunger element which advances the drug within tissue penetrating member lumen and also forms a seal with the lumen. The plunger element can be integral or attached to the delivery member. Preferably, the delivery member is configured to travel a fixed distance within the needle lumen so as to deliver a fixed or metered dose of drug into the intestinal wall. This can be achieved by one or more of the selection of the diameter of the delivery member (e.g., the diameter can be distally tapered), the diameter of the tissue penetrating member (which can be narrowed at its distal end), use of a stop, and/or the actuating mechanism. For embodiments of the device having a tissue penetrating member fabricated from drug (e.g., a drug dart), the delivery member is adapted to advance the dart out of the capsule and into tissue.

The delivery member and tissue penetrating member can be configured for the delivery of liquid, semi-liquid or solid forms of drug or all three. Solid forms of drug can include both powder or pellet. Semi liquid can include a slurry or paste. The drug can be contained within a cavity of the capsule, or in the case of the liquid or semi-liquid, within an enclosed reservoir. In some embodiments, the capsule can include a first second, or a third drug (or more). Such drugs can be contained within the tissue penetrating member lumen (in the case of solids or powder) or in separate reservoirs within the capsule body.

The actuating mechanism can be coupled to at least one of the tissue penetrating member or the delivery member. The actuating mechanism is configured to advance the tissue penetrating member a selectable distance into the intestinal wall as well as advance the delivery member to deliver the drug and then withdraw the tissue penetrating member from the intestinal wall. In various embodiments, the actuating mechanism can comprise a preloaded spring mechanism which is configured to be released by the release element. Suitable springs can include both coil (including conical shaped springs) and leaf springs with other spring structures also contemplated. In particular embodiments, the spring can be cone shaped to reduce the length of the spring in the compressed state even to the point where the compressed length of the spring is about the thickness of several coils (e.g., two or three) or only one coil.

In particular embodiments the actuating mechanism comprises a spring, a first motion converter, and a second motion converter and a track member. The release element is coupled to the spring to retain the spring in a compressed state such that degradation of the release element releases the spring. The first motion converter is configured to convert motion of the spring to advance and withdraw the tissue penetrating element in and out of tissue. The second motion converter is configured to convert motion of the spring to advance the delivery member into the tissue penetrating member lumen. The motion converters are pushed by the spring and ride along a rod or other track member which serves to guide the path of the converters. They engage the tissue penetrating member and/or delivery member (directly or indirectly) to produce the desired motion. They are desirably configured to convert motion of the spring along its longitudinal axis into orthogonal motion of the tissue penetrating member and/or delivery member though conversion in other directions is also contemplated. The motion converters can have a wedge, trapezoidal or curved shape with other shapes also contemplated. In particular embodiments, the first motion converter can have a trapezoidal shape and include a slot which engages a pin on the tissue penetrating member that rides in the slot. The slot can have a trapezoidal shape that mirrors or otherwise corresponds to the overall shape of the converter and serves to push the tissue penetrating member during the upslope portion of the trapezoid and then pull it back during the down slope portion. In one variation, one or both of the motion converters can comprise a cam or cam like device which is turned by the spring and engages the tissue penetrating and/or delivery member.

In other variations, the actuating mechanism can also comprise an electro-mechanical device/mechanism such as a solenoid, or a piezoelectric device. In one embodiment, the piezoelectric device can comprise a shaped piezoelectric element which has a non-deployed and deployed state. This element can be configured to go into the deployed state upon the application of a voltage and then return to the non-deployed state upon the removal of the voltage. This and related embodiments allow for a reciprocating motion of the actuating mechanism so as to both advance the tissue penetrating member and then withdraw it.

The release element is coupled to at least one of the actuating mechanism or a spring coupled to the actuating mechanism. In particular embodiments, the release element is coupled to a spring positioned within the capsule so as to retain the spring in a compressed state. Degradation of the release element releases the spring to actuate the actuation mechanism. In many embodiments, the release element comprises a material configured to degrade upon exposure to chemical conditions in the small or large intestine such as pH. Typically, the release element is configured to degrade upon exposure to a selected pH in the small intestine, e.g., 7.0, 7.1, 7.2, 7.3, 7.4, 8.0 or greater. However, it can also be configured to degrade in response to other conditions in the small intestine. In particular embodiments, the release element can be configured to degrade in response to particular chemical conditions in the fluids in the small intestine such as those which occur after ingestion of a meal (e.g., a meal high in fats or proteins).

Biodegradation of the release element from one or more conditions in the small intestine (or other location in the GI tract) can be achieved by selection of the materials for the release element, the amount of cross linking of those materials as well as the thickness and other dimensions of the release elements. Lesser amounts of cross linking and or thinner dimensions can increase the rate of degradation and visa versa. Suitable materials for the release element can comprise biodegradable materials such as various enteric materials which are configured to degrade upon exposure to the higher pH or other condition in the small intestine. The enteric materials can be copolymerized or otherwise mixed with one or more polymers to obtain a number of particular material properties in addition to biodegradation. Such properties can include without limitation stiffness, strength, flexibility and hardness.

In particular embodiments, the release element can comprise a film or plug that fits over or otherwise blocks the guide tube and retains the tissue penetrating member inside the guide tube. In these and related embodiments, the tissue penetrating member is coupled to a spring loaded actuating mechanism such that when the release element is degraded sufficiently, it releases the tissue penetrating member which then springs out of the guide tube to penetrate into the intestinal wall. In other embodiments, the release element can be shaped to function as a latch which holds the tissue penetrating element in place. In these and related embodiments, the release element can be located on the exterior or the interior of the capsule. In the interior embodiments, the capsule and guide tubes are configured to allow for the ingress of intestinal fluids into the capsule interior to allow for the degradation of the release element.

In some embodiments, the actuating mechanism can be actuated by means of a sensor, such as a pH or other chemical sensor which detects the presence of the capsule in the small intestine and sends a signal to the actuating mechanism (or to an electronic controller coupled to the actuating mechanism to actuate the mechanism). Embodiments of a pH sensor can comprise an electrode-based sensor or it can be a mechanically-based sensor such as a polymer which shrinks or expands upon exposure to the pH or other chemical conditions in the small intestine. In related embodiments, an expandable/contractable sensor can also comprise the actuating mechanism itself by using the mechanical motion from the expansion or contraction of the sensor.

According to another embodiment for detecting that the device is in the small intestine (or other location in the GI tract), the sensor can comprise a strain gauge or other pressure/force sensor for detecting the number of peristaltic contractions that the capsule is being subject to within a particular location in the intestinal tract. In these embodiments, the capsule is desirably sized to be gripped by the small intestine during a peristaltic contraction). Different locations within the GI tract have different number of peristaltic contractions. The small intestine has between 12 to 9 contractions per minute with the frequency decreasing down the length of the intestine. Thus, according to one or more embodiments detection of the number of peristaltic contractions can be used to not only determine if the capsule is in the small intestine but the relative location within the intestine as well.

As an alternative or supplement to internally activated drug delivery, in some embodiments, the user may externally activate the actuating mechanism to deliver drug by means of RF, magnetic or other wireless signaling means known in the art. In these and related embodiments, the user can use a handheld device (e.g., a hand held RF device) which not only includes signaling means, but also means for informing the user when the device is in the small intestine or other location in the GI tract. The later embodiment can be implemented by including an RF transmitter on the swallowable device to signal to the user when the device is in the small intestine or other location (e.g., by signaling an input from the sensor). The same handheld device can also be configured to alter the user when the actuating mechanism has been activated and the selected drug(s) delivered. In this way, the user is provided confirmation that the drug has been delivered. This allows the user to take other appropriate drugs/therapeutic agents as well as make other related decisions (e.g., for diabetics to eat a meal or not and what foods should be eaten). The handheld device can also be configured to send a signal to the swallowable device to over-ride the actuating mechanism and so prevent, delay or accelerate the delivery of drug. In use, such embodiments allow the user to intervene to prevent, delay or accelerate the delivery of drug based upon other symptoms and/or patient actions (e.g., eating a meal, deciding to go to sleep, exercise etc).

The user may also externally activate the actuating mechanism at a selected time period after swallowing the capsule. The time period can be correlated to a typical transit time or range of transit times for food moving through the user's GI tract to a particular location in the tract such as the small intestine.

Another aspect of the inventions provides therapeutic agent preparations for delivery into the wall of the small intestine (or other wall of a lumen in the intestinal tract) using embodiments of the swallowable device described herein. The preparation comprises a therapeutically effective dose of at least one therapeutic agent (e.g., insulin, an anti-seizure compound, non-steroidal anti-inflammatory drugs, an antibiotic etc). It may comprise a solid, liquid or combination of both and can include one or more pharmaceutical excipients. The preparation has a shape and material consistency to be contained in embodiments of the swallowable capsule, delivered from the capsule into the lumen wall and degrade within the lumen wall to release the dose of therapeutic agent. The preparation may also have a selectable surface area to volume ratio so as enhance or otherwise control the rate of degradation of the preparation in the wall of the small intestine or other body lumen. In various embodiments, the preparation can be configured to be coupled to an actuator such as a release element or actuation mechanism which has a first configuration in which the preparation is contained in the capsule and a second configuration in which the preparation is advanced out of the capsule and into the wall of the small intestine. The dose of the drug or other therapeutic agent in the preparation can be titrated downward from that which would be required for conventional oral delivery methods so that potential side effects from the drug can be reduced.

Typically, though not necessarily, the preparation will be shaped and otherwise configured to be contained in the lumen of a tissue penetrating member, such as a hollow needle which is configured to be advanced out of the capsule and into the wall of the small intestine. The preparation itself may comprise a tissue penetrating member configured to be advanced into the wall of the small intestine or other lumen in the intestinal tract.

Another aspect of the invention provides methods for the delivery of drugs and the therapeutic agents into the walls of the GI tract using embodiments of the swallowable drug delivery devices. Such methods can be used for the delivery of therapeutically effective amounts of a variety of drugs and other therapeutic agents. These include a number of large molecule peptides and proteins which would otherwise require injection due to chemical breakdown in the stomach e.g., growth hormone, parathyroid hormone, insulin, interferons and other like compounds. Suitable drugs and other therapeutic agents which can be delivered by embodiments of invention include various chemotherapeutic agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents, immune suppression agents and anti-parasitic agents such as various anti-malarial agents. The dosage of the particular drug can be titrated for the patient's weight, age, condition or other parameter.

In various method embodiments, embodiments of the drug swallowable drug delivery device can be used to deliver a plurality of drugs for the treatment of multiple conditions or for the treatment of a particular condition (e.g., a mixture of protease inhibitors for treatment HIV AIDS). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream at about the same time. Due to differences in chemical makeup, molecular weight, etc, drugs can be absorbed through the intestinal wall at different rates, resulting in different pharmacokinetic distribution curves. Embodiments of the invention address this issue by injecting the desired drug mixtures at about the same time. This in turn improves pharmacokinetics and thus, the efficacy of the selected mixture of drugs.

Further details of these and other embodiments and aspects of the invention are described more fully below, with reference to the attached drawing figures.

BRIEF DESCRIPTION OF THE DRAWINGS

FIG. 8a shows the device in the small intestine prior to deployment of the tissue penetrating members with the release element in tact; FIG. 8b shows the device in the small intestine with the release element degraded and the tissue penetrating elements deployed; and FIG. 8c shows the device in the small intestine with the tissue penetrating elements retracted and the drug delivered.

DETAILED DESCRIPTION OF THE INVENTION

Figure 1A:
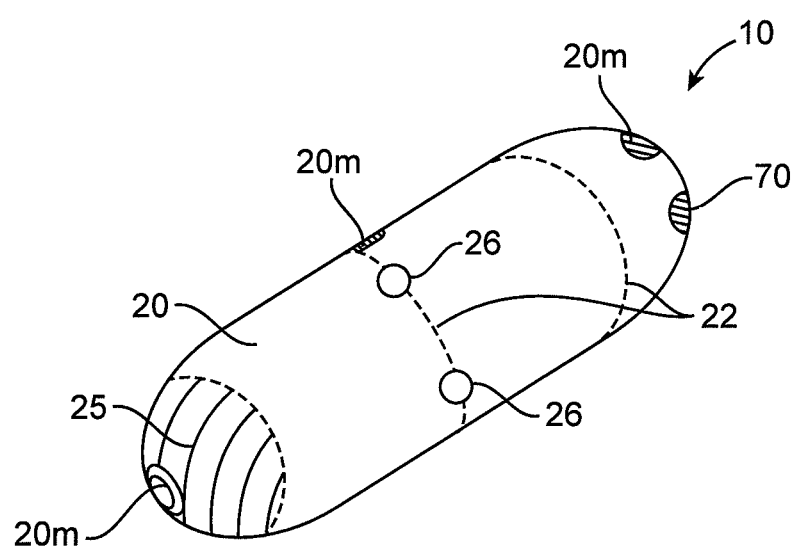
FIG. 1a is a lateral viewing showing an embodiment of a swallowable drug delivery device.

Embodiments of the invention provide devices, systems and methods for delivering medications in to various locations in the body. As used herein, the term "medication" refers to a medicinal preparation in any form which can include drugs or other therapeutic agents as well as one or more pharmaceutical excipients. Many embodiments provide a swallowable device for delivering medication within the GI tract. Particular embodiments provide a swallowable device such as a capsule for delivering medications to the wall of the small intestine or other GI organ.

Referring now to FIGS. 1-11, an embodiment of an device 10 for the delivery of medication 100 to a delivery site DS in the intestinal tract, comprises a capsule 20 including at least one guide tube 30, one or more tissue penetrating members 40 positioned or otherwise advanceable in the at least one guide tube, a delivery member 50, an actuating mechanism 60 and release element 70. Medication 100, also described herein as preparation 100, typically comprises at least one drug or therapeutic agent 101 and may include one or more pharmaceutical excipients known in the art.

Figure 1B:
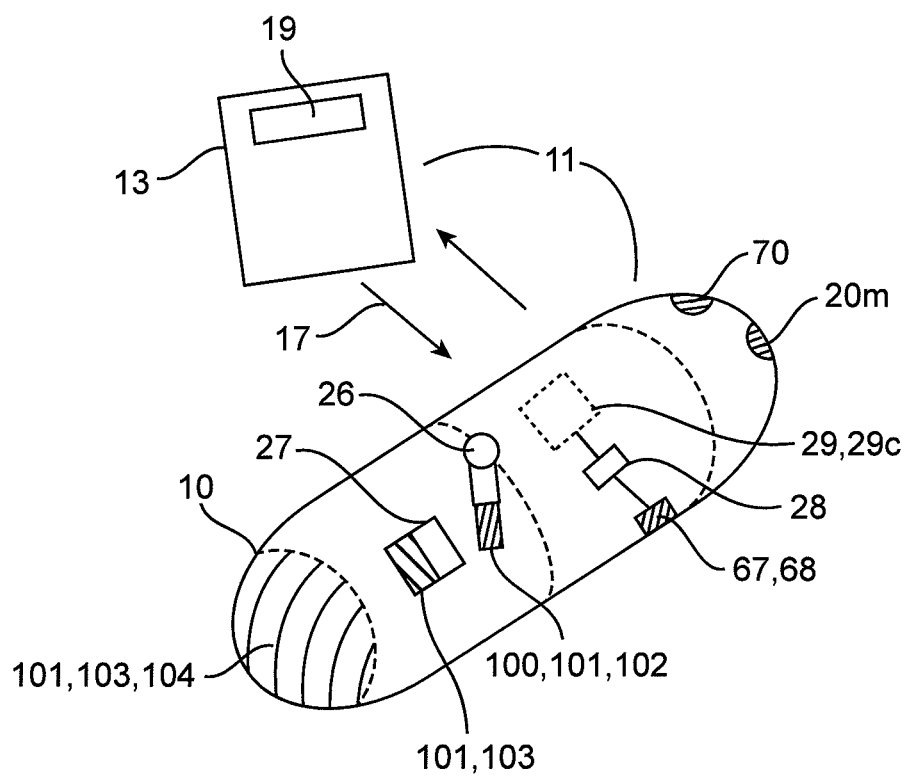
FIG. 1b is a lateral viewing showing an embodiment of a system including a swallowable drug delivery device.

Device 10 can be configured for the delivery of liquid, semi-liquid or solid forms of medication 100 or all three. Solid forms of medication/preparation 100 can include both powder or pellet. Semi liquid forms can include a slurry or paste. Whatever the form, preparation 100 desirably has a shape and material consistency allowing the medication to be advanced out of the device, into the intestinal wall (or other luminal wall in the GI tract) and then degrade in the intestinal wall to release the drug or other therapeutic agent 101. The material consistency can include one or more of the hardness, porosity and solubility of the preparation (in body fluids). The material consistency can be achieved by one or more of the following: i) the compaction force used to make the preparation; ii) the use of one or more pharmaceutical disintegrants known in the art; iii) use of other pharmaceutical excipients; iv) the particle size and distribution of the preparation (e.g., micronized particles); and v) use of micronizing and other particle formation methods known in the art. Suitable shapes for preparation 100 can include cylindrical, cubical, rectangular, conical, spherical, hemispherical and combinations thereof. Also, the shape can be selected so as to define a particular surface area and volume of preparation 100 and thus, the ratio between the two. The ratio of surface area to volume can in turn, be used to achieve a selected rate of degradation within the intestinal or other lumen wall. Larger ratios (e.g., larger amounts of surface area per unit volume) can be used to achieve faster rates of degradation and vice versa. In particular embodiments, the surface area to volume ratio can be in the range of about 1:1 to 100:1, with specific embodiments of 2:1, 5:1, 20:1, 25:1, 50:1 and 75:1. Preparation/medication 100 will typically be pre-packed within a lumen 44 of tissue penetrating members 40, but can also be contained at another location within an interior 24 of capsule 20, or in the case of a liquid or semi-liquid, within an enclosed reservoir 27. The medication can be pre-shaped to fit into the lumen or packed for example, in a powder form. Typically, the device 10 will be configured to deliver a single drug 101 as part of medication 100. However in some embodiments, the device 10 can be configured for delivery of multiple drugs 101 including a first second, or a third drug which can be compounded into a single or multiple medications 100. For embodiments having multiple medications/drugs, the medications can be contained in separate tissue penetrating members 40 or within separate compartments or reservoirs 27 within capsule 20. In another embodiment, a first dose 102 of medication 100 containing a first drug 101 can be packed into the penetrating member(s) 40 and a second dose 103 of medication 100 (containing the same or a different drug 101) can be coated onto the surface 25 of capsule as is shown in the embodiment of FIG. 1b. The drugs 101 in the two doses of medication 102 and 103 can be the same or different. In this way, a bimodal pharmacokinetic release of the same or different drugs can be achieved. The second dose 103 of medication 100 can have an enteric coating 104 to ensure that it is released in the small intestine and achieve a time release of the medication 100 as well. Enteric coating 104 can include one or more enteric coatings described herein or known in the art.

Figure 1C:
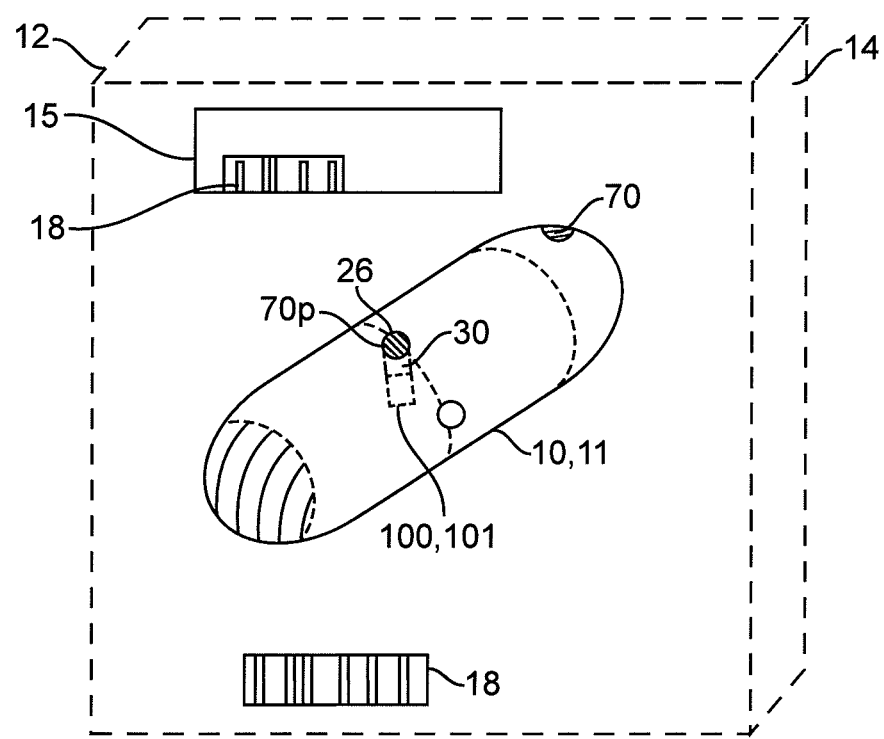
FIG. 1c is a lateral viewing showing an embodiment of a kit including a swallowable drug delivery device and a set of instructions for use.
Figure 1D:
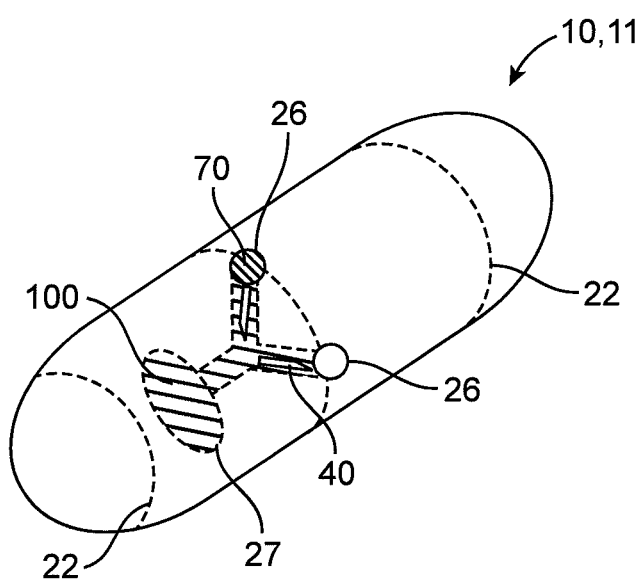
FIG. 1d is a lateral viewing showing an embodiment of a swallowable drug delivery device including a drug reservoir.

A system 11 for delivery of medication 100 into the wall of the small intestine or other location within the GI tract, may comprise device 10, containing one or more medications 100 for the treatment of a selected condition or conditions. In some embodiments, the system may include a hand held device 13, described herein for communicating with device 10 as is shown in the embodiment of FIG. 1b. System 11 may also be configured as a kit 14 including system 11 and a set of instructions for use 15 which are packaged in packaging 12 as is shown in the embodiment of FIG. 1c. The instructions can indicate to the patient when to take the device 10 relative to one or more events such as the ingestion of a meal or a physiological measurement such as blood glucose, cholesterol, etc. In such embodiments, kit 14 can include multiple devices 10 containing a regimen of medications 100 for a selected period of administration, e.g., a day, week, or multiple weeks depending upon the condition to be treated.

Capsule 20 is sized to be swallowed and pass through the intestinal tract. The size can also be adjusted depending upon the amount of drug to be delivered as well as the patient's weight and adult vs. pediatric applications. Capsule 20 includes an interior volume 24 and an outer surface 25 having one or more apertures 26 sized for guide tubes 30. In addition to the other components of device 10, (e.g., the actuation mechanism etc.) the interior volume can include one or more compartments or reservoirs 27. One or more portions of capsule 20 can be fabricated from various biocompatible polymers known in the art, including various biodegradable polymers which in a preferred embodiment can comprise PGLA (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof. As is described in further detail herein, in various embodiments, capsule 20 can include seams 22 of bio-degradable material so as to controllably degrade into smaller pieces 23 which are more easily passed through the intestinal tract. Additionally, in various embodiments, the capsule can include various radio-opaque or echogenic materials for location of the device using fluoroscopy, ultrasound or other medical imaging modality. In specific embodiments, all or a portion of the capsule can include radio-opaque/echogenic markers 20m as is shown in the embodiment of FIGS. 1a and 1b. In use, such materials not only allow for the location of device 10 in the GI tract, but also allow for the determination of transit times of the device through the GI tract.

In preferred embodiments, tissue penetrating members 40 are positioned within guide tubes 30 which serve to guide and support the advancement of members 40 into tissue such as the wall of the small intestine or other portion of the GI tract. The tissue penetrating members 40 will typically comprise a hollow needle or other like structure and will have a lumen 44 and a tissue penetrating end 45 for penetrating a selectable depth into the intestinal wall IW. Member 40 may also include a pin 41 for engagement with a motion converter 90 described herein. The depth of penetration can be controlled by the length of member 40, the configuration of motion converter 90 described herein as well as the placement of a stop or flange 40s on member 40 which can, in an embodiment, correspond to pin 41 described herein. Medication 100 will typically be delivered into tissue through lumen 44. In many embodiments, lumen 44 is pre-packed with the desired medication 100 which is advanced out of the lumen using delivery member 50 or other advancement means (e.g. by means of force applied to a collapsible embodiment of member 40). As an alternative, medication 100 can be advanced into lumen 44 from another location/compartment in capsule 20. In some embodiments, all or a portion of the tissue penetrating member 40 can be fabricated from medication 100 itself In these and related embodiments, the medication can have a needle or dart-like structure (with or without barbs) configured to penetrate and be retained in the intestinal wall, such as the wall of the small intestine. The dart can be sized and shaped depending upon the medication, dose and desired depth of penetration into the intestinal wall. Medication 100 can be formed into darts, pellets or other shapes using various compression molding methods known in the pharmaceutical arts.

Figure 7A:
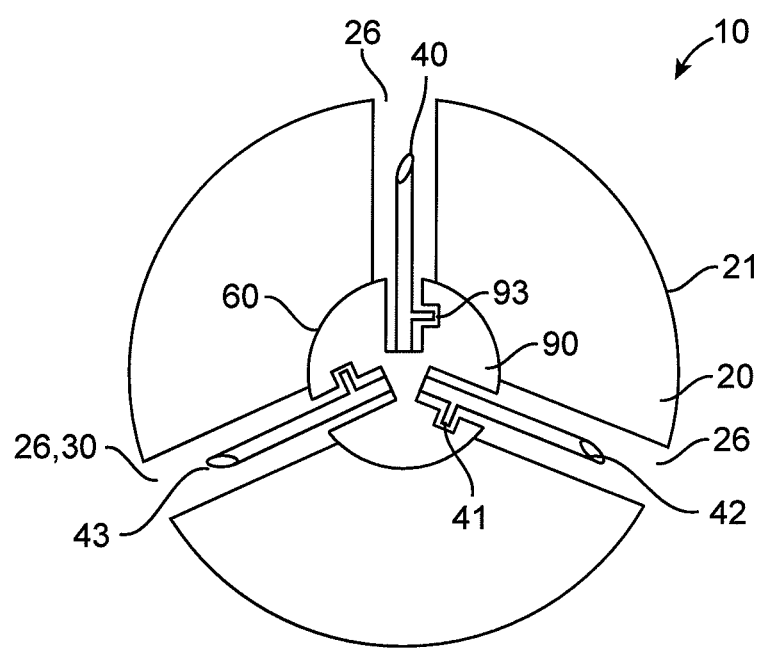
FIG. 7a is a cross sectional view illustrating an embodiment of the swallowable drug delivery device having multiple tissue penetrating members and an actuating mechanism for advancing the tissue penetrating members.
Figure 7B:
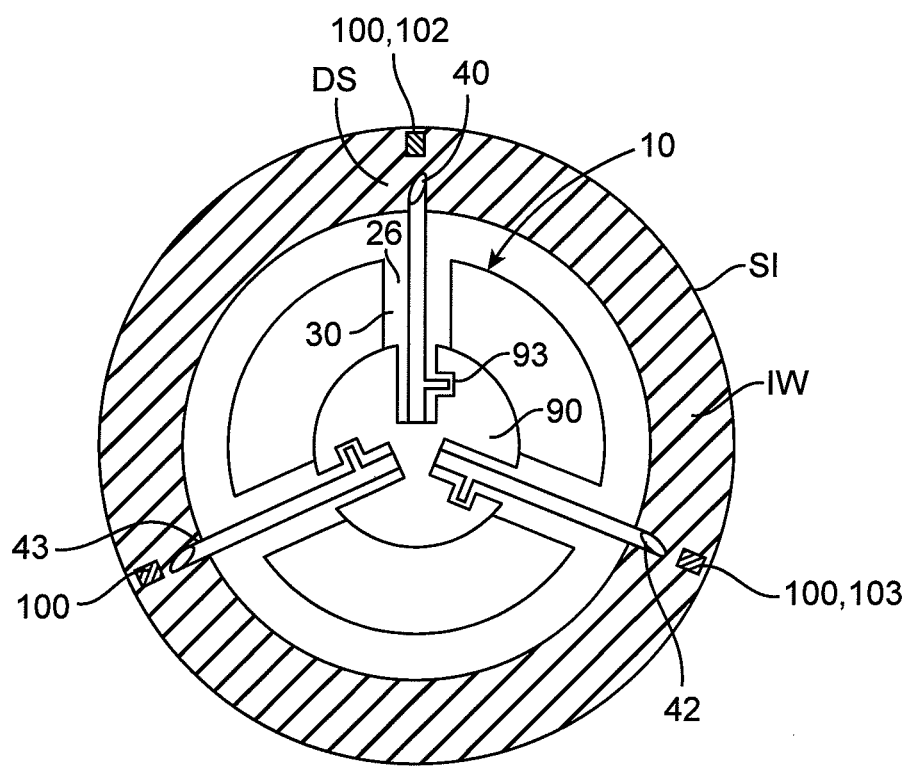
FIG. 7b is a cross sectional view illustrating deployment of the tissue penetrating members of the embodiment of FIG. 7a to deliver medication to a delivery site and anchor the device in the intestinal wall during delivery.
Figure 8A:
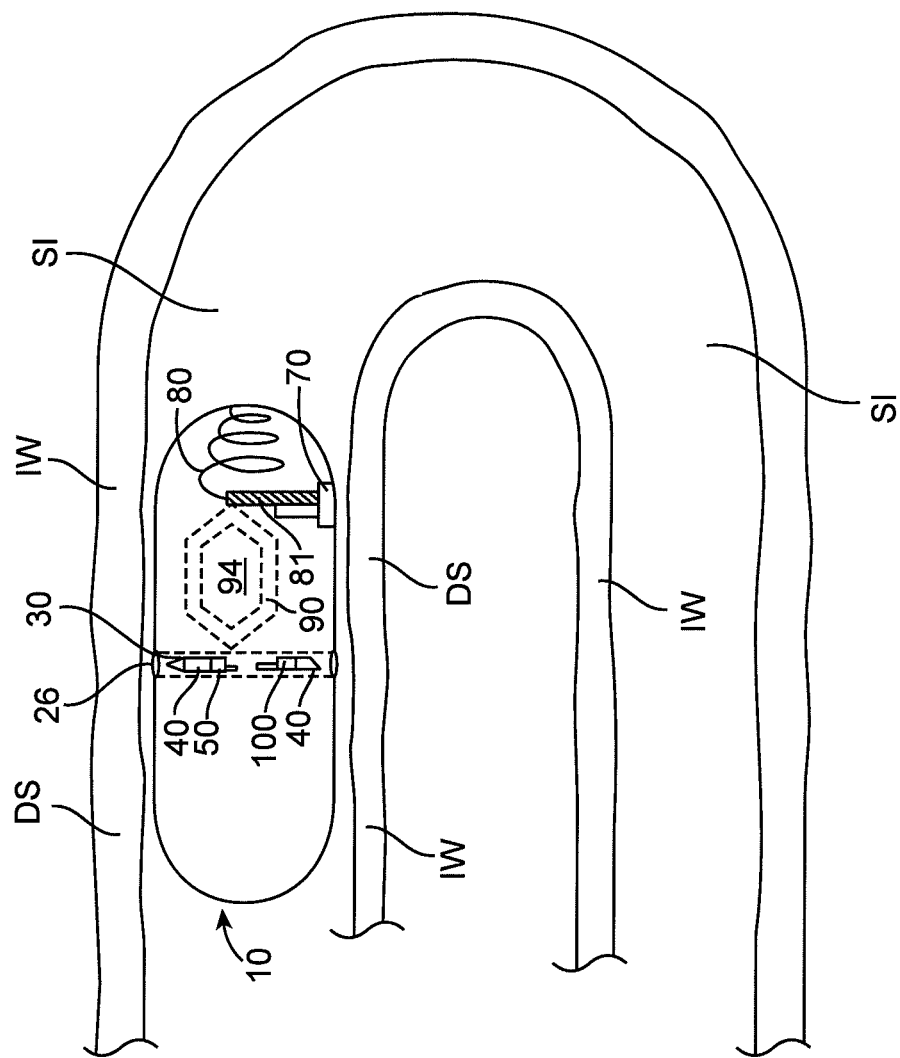
FIGS. 8a-8c are side view illustrating positioning of the drug delivery device in the small intestine and deployment of the tissue penetrating members to deliver drug.
Figure 8B:
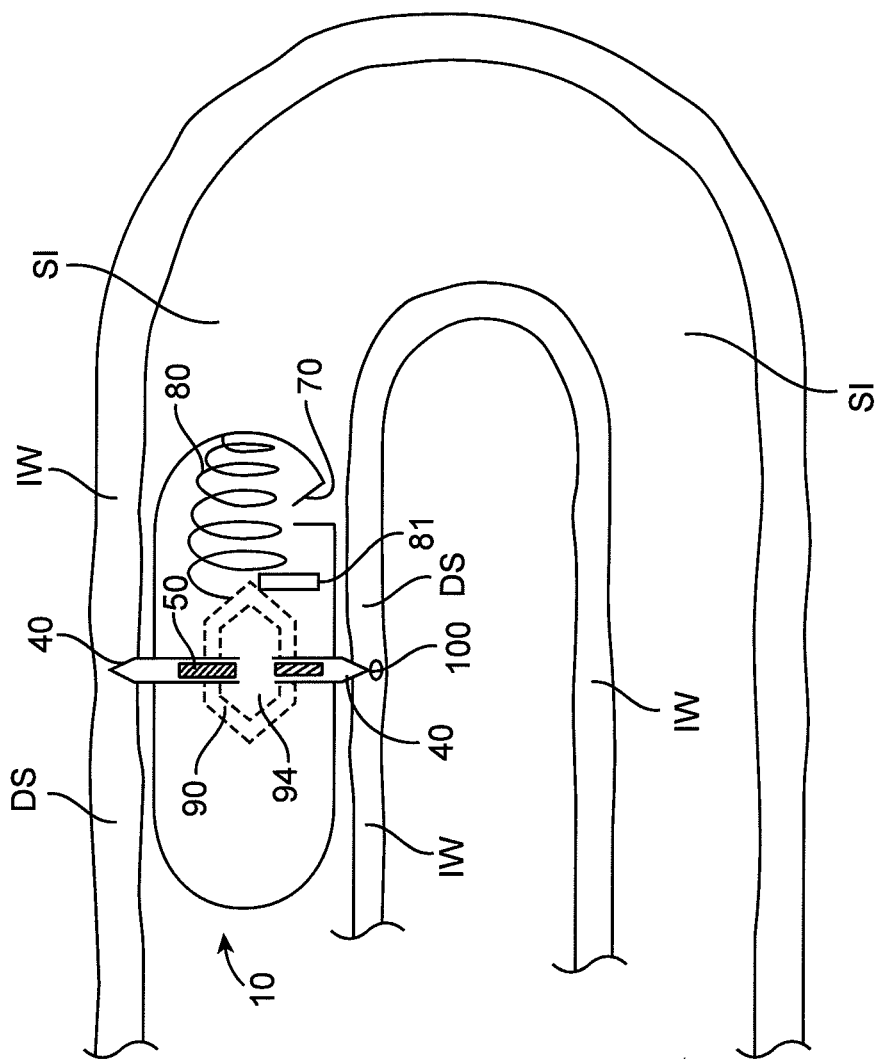
Figure 8C:
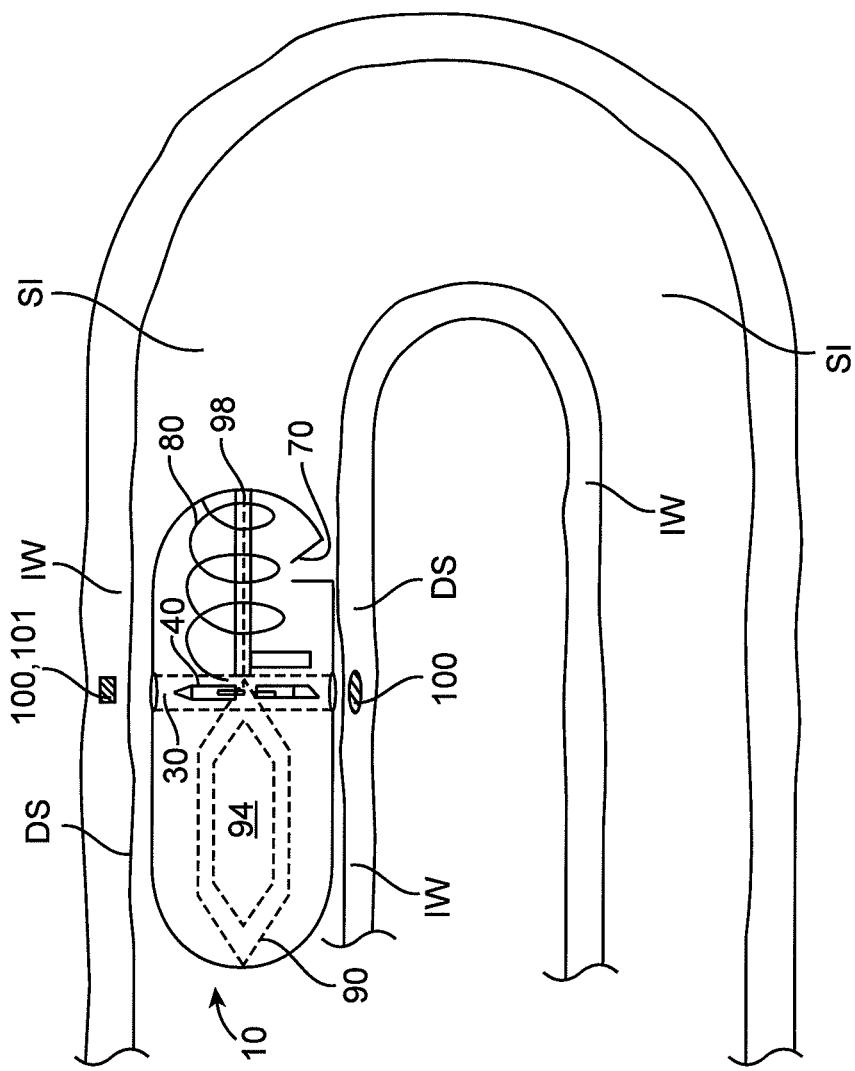

In various embodiments, device 10 can include a second 42 and a third 43 tissue penetrating member 40 as is shown in the embodiments of FIGS. 7a and 7b, with additional numbers contemplated. Each tissue penetrating member 40 can be used to deliver the same or a different medication 100. In preferred embodiments, the tissue penetrating members 40 can be substantially symmetrically distributed around the perimeter 21 of capsule 20 so as to anchor the capsule onto the intestinal wall IW during delivery of medications 100. Anchoring capsule 20 in such a way reduces the likelihood that the capsule will be displaced or moved by peristaltic contractions occurring during delivery of the medication. In specific embodiments, the amount of anchoring force can be adjusted to the typical forces applied during peristaltic contraction of the small intestine. Anchoring can be further facilitated by configured some or all of tissue penetrating members 40 to have a curved or arcuate shape.

Delivery member 50 is configured to advance medication 100 through the tissue penetrating member lumen 44 and into the intestinal wall IW. Accordingly, at least a portion of the delivery member 50 is advanceable within the tissue penetrating member lumen 44 and thus member 50 has a size and shape (e.g., a piston like shape) configured to fit within the delivery member lumen 44.

In some embodiments, the distal end 50d of the delivery member (the end which is advanced into tissue) can have a plunger element 51 which advances the medication within the tissue penetrating member lumen 44 and also forms a seal with the lumen. Plunger element 51 can be integral or attached to delivery member 50. Preferably, delivery member 50 is configured to travel a fixed distance within the needle lumen 44 so as to deliver a fixed or metered dose of drug into the intestinal wall IW. This can be achieved by one or more of the selection of the diameter of the delivery member (e.g., the diameter can be distally tapered), the diameter of the tissue penetrating member (which can be narrowed at its distal end), use of a stop, and/or the actuating mechanism. However in some embodiments, the stroke or travel distance of member 50 can be adjusted in situ responsive to various factors such as one or more sensed conditions in the GI tract. In situ adjustment can be achieved through use of logic resource 29 (including controller 29c) coupled to an electro-mechanical embodiment of actuating mechanism 60. This allows for a variable dose of medication and/or variation of the distance the medication is injected into the intestinal wall.

Actuating mechanism 60 can be coupled to at least one of the tissue penetrating member 40 or delivery member 50. The actuating mechanism is configured to advance tissue penetrating member 40 a selectable distance into the intestinal wall IW as well as advance the delivery member to deliver medication 100 and then withdraw the tissue penetrating member from the intestinal wall. In various embodiments, actuating mechanism 60 can comprise a spring loaded mechanism which is configured to be released by release element 70. Suitable springs 80 can include both coil (including conical shaped springs) and leaf springs with other spring structures also contemplated. In particular embodiments, spring 80 can be substantially cone-shaped to reduce the length of the spring in the compressed state even to the point where the compressed length of the spring is about the thickness of several coils (e.g., two or three) or only one coil.

Figure 2:
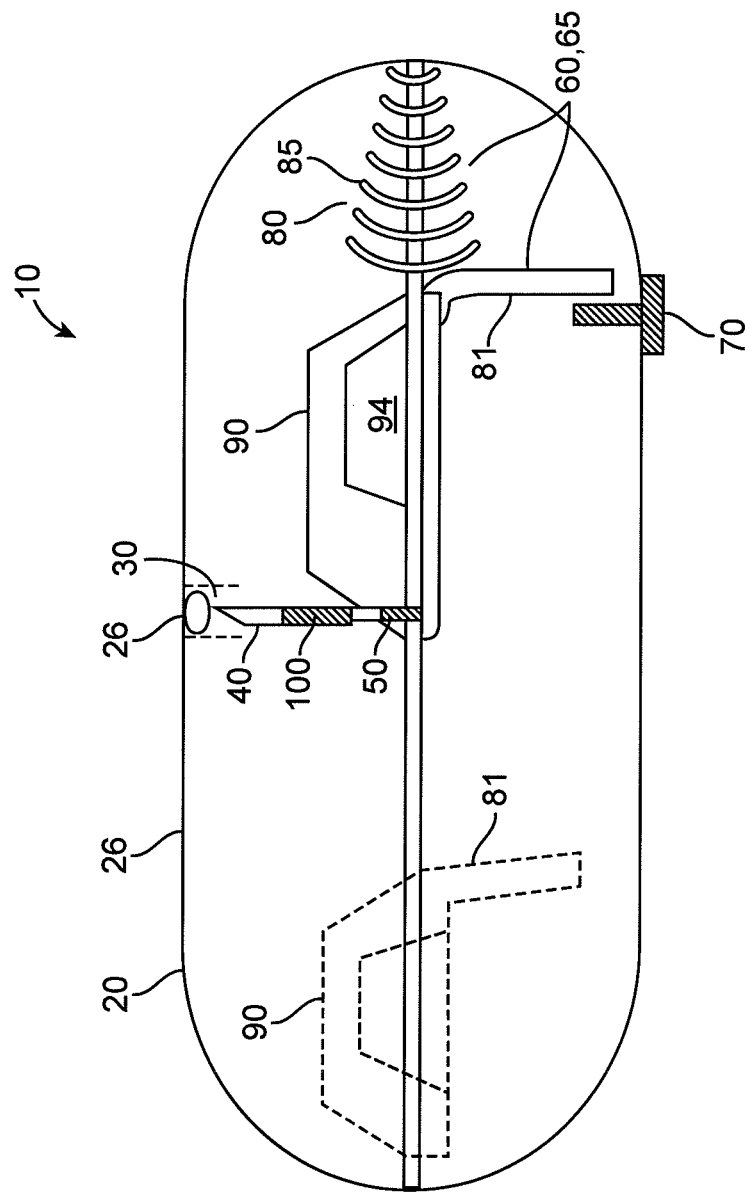
FIG. 2 is a lateral view illustrating an embodiment of the swallowable drug delivery device having a spring loaded actuation mechanism for advancing tissue penetrating members into tissue.
Figure 3:
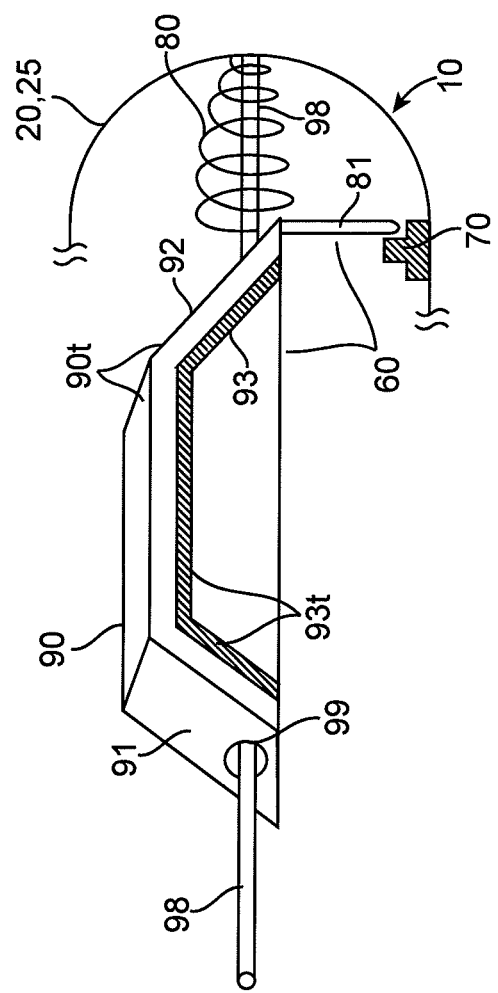
FIG. 3 is a lateral view illustrating an embodiment of the swallowable drug delivery device having a spring loaded actuation mechanism having a first motion converter.
Figure 4:
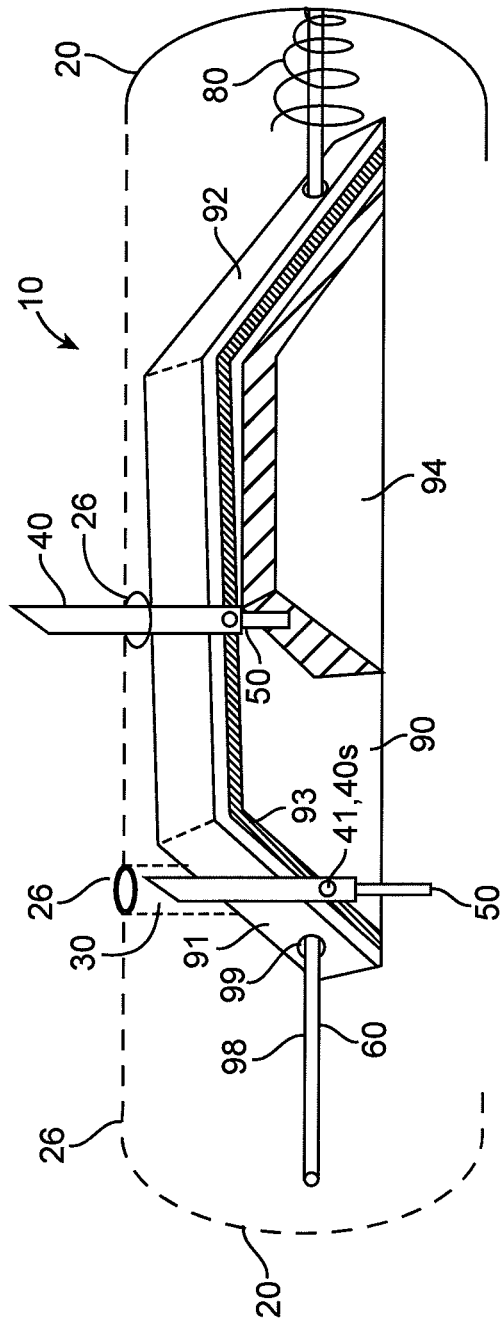
FIG. 4 is a lateral view illustrating an embodiment of the swallowable drug delivery device having a spring loaded actuation mechanism having first and a second motion converter.
Figure 5:
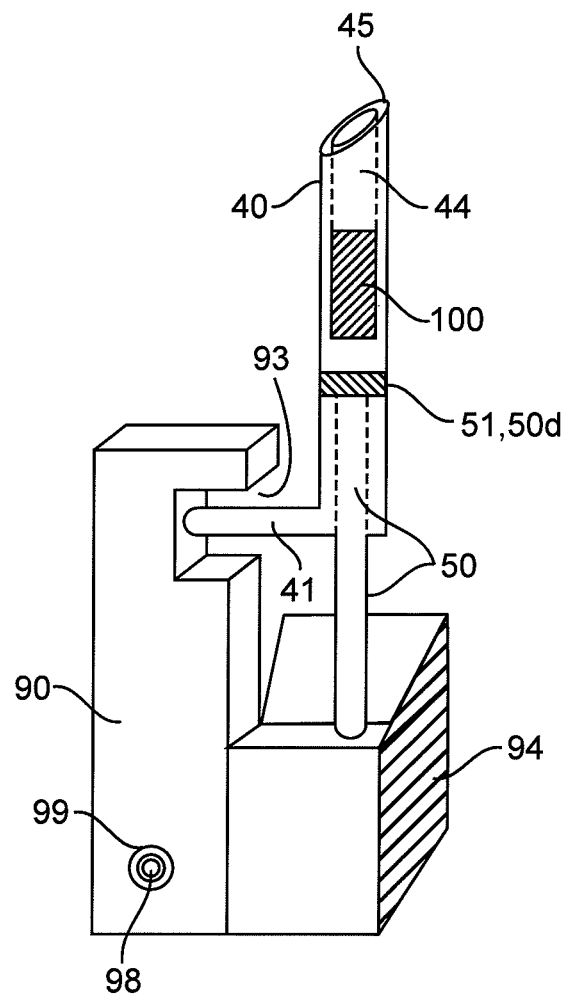
FIG. 5 is a perspective view illustrating engagement of the first and second motion converters with the tissue penetrating member and delivery members.
Figure 6:
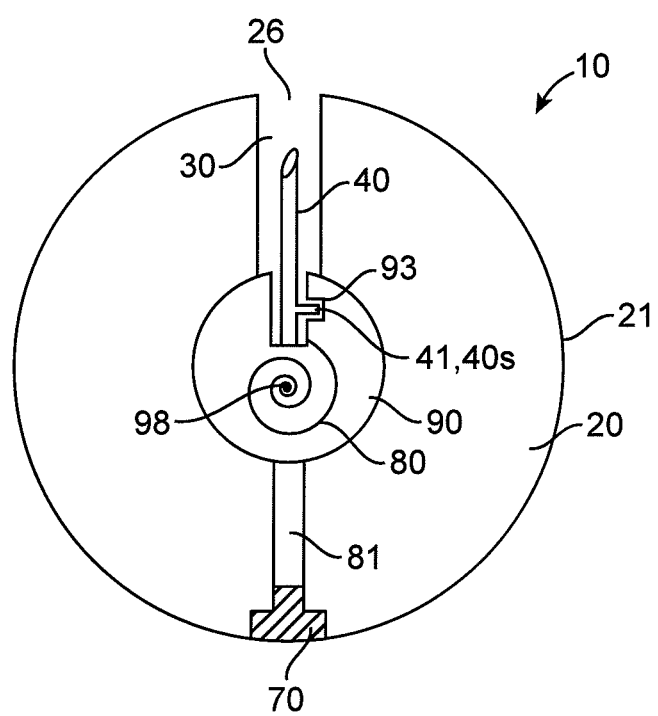
FIG. 6 is a cross sectional view illustrating an embodiment of the swallowable drug delivery device having a single tissue penetrating member and an actuating mechanism for advancing the tissue penetrating member.

In particular embodiments actuating mechanism 60 can comprise a spring 80, a first motion converter 90, and a second motion converter 94 and a track member 98 as is shown in the embodiments of FIGS. 2, 4 and 8a-8c. The release element 70 is coupled to spring 80 to retain the spring in a compressed state such that degradation of the release element releases the spring. Spring 80 may be coupled to release element 70 by a latch or other connecting element 81. First motion converter 90 is configured to convert motion of spring 80 to advance and withdraw the tissue penetrating member 40 in and out of the intestinal wall or other tissue. The second motion converter 94 is configured to convert motion of the spring 80 to advance the delivery member 50 into the tissue penetrating member lumen 44. Motion converters 90 and 94 are pushed by the spring and ride along a rod or other track member 98 which fits into a track member lumen 99 of converter 90. The track member 98 serves to guide the path of the converters 90. Converters 90 and 94 engage the tissue penetrating member 40 and/or delivery member 50 (directly or indirectly) to produce the desired motion. They have a shape and other characteristics configured to convert motion of the spring 80 along its longitudinal axis into orthogonal motion of the tissue penetrating member 40 and/or delivery member 50 though conversion in other directions is also contemplated. The motion converters can have a wedge, trapezoidal or curved shape with other shapes also contemplated. In particular embodiments, the first motion converter 90 can have a trapezoidal shape 90t and include a slot 93 which engages a pin 41 on the tissue penetrating member that rides in the slot as is shown in the embodiments of FIGS. 2, 3 and 4. Slot 93 can also have a trapezoidal shape 93t that mirrors or otherwise corresponds to the overall shape of converter 90. Slot 93 serves to push the tissue penetrating member 40 during the upslope portion 91 of the trapezoid and then pull it back during the down slope portion 92. In one variation, one or both of the motion converters 90 and 94 can comprise a cam or cam like device (not shown). The cam can be turned by spring 80 so as to engage the tissue penetrating and/or delivery members 40 and 50. One or more components of mechanism 60 (as well as other components of device 10) including motion converters 90 and 94 can be fabricated using various MEMS-based methods known in the art so as to allow for selected amounts of miniaturization to fit within capsule 10. Also as is described herein, they can be formed from various biodegradable materials known in the art.

In other variations, the actuating mechanism 60 can also comprise an electro-mechanical device/mechanism such as a solenoid, or a piezoelectric device. In one embodiment, a piezoelectric device used in mechanism 60 can comprise a shaped piezoelectric element which has a non-deployed and deployed state. This element can be configured to go into the deployed state upon the application of a voltage and then return to the non-deployed state upon the removal of the voltage. This and related embodiments allow for a reciprocating motion of the actuating mechanism 60 so as to both advance the tissue penetrating member and then withdraw it. The voltage for the piezoelectric element can be obtained generated using a battery or a piezoelectric based energy converter which generates voltage by mechanical deformation such as that which occurs from compression of the capsule 20 by a peristaltic contraction of the small intestine around the capsule. Further description of piezoelectric based energy converters is found in U.S. patent application Ser. No. 12/556,524 which is fully incorporated by reference herein for all purposes. In one embodiment, deployment of tissue penetrating members 40 can in fact be triggered from a peristaltic contraction of the small intestine which provides the mechanical energy for generating voltage for the piezoelectric element.

Release element 70 will typically be coupled to the actuating mechanism 60 and/or a spring coupled to the actuating mechanism; however, other configurations are also contemplated. In preferred embodiments, release element 70 is coupled to a spring 80 positioned within capsule 20 so as to retain the spring in a compressed state 85 as shown in the embodiment of FIG. 2. Degradation of the release element 70 releases spring 80 to actuate actuation mechanism 60. Accordingly, release element 70 can thus function as an actuator 70a (actuator 70 may also include spring 80 and other elements of mechanism 60). As is explained further below, release element 70/actuator 70a has a first configuration where the therapeutic agent preparation 100 is contained within capsule 20 and a second configuration where the therapeutic agent preparation is advanced from the capsule into the wall of the small intestine or other luminal wall in the intestinal tract.

In many embodiments, release element 70 comprises a material configured to degrade upon exposure to chemical conditions in the small or large intestine such as pH. Typically, release element 70 is configured to degrade upon exposure to a selected pH in the small intestine, e.g., 7.0, 7.1, 7.2, 7.3, 7.4, 7.5, 7.6 8.0 or greater. The release element can also be configured to degrade within a particular range of pH such as, e.g., 7.0 to 7.5. In particular embodiments, the pH at which release element 70 degrades (defined herein as the degradation pH) can be selected for the particular drug to be delivered so as to release the drug at a location in small intestine which corresponds to the selected pH. Further, for embodiments of device 10 having multiple medications 100, the device can include a first release element 70 (coupled to an actuating mechanism for delivering a first drug) configured to degrade at first pH and a second release element 70 (coupled to an actuating mechanism for delivering a second drug) configured to degrade at a second pH (with additional numbers of release elements contemplated for varying number of drugs).

Release element 70 can also be configured to degrade in response to other conditions in the small intestine (or other GI location). In particular embodiments, the release element 70 can be configured to degrade in response to particular chemical conditions in the fluids in the small intestine such as those which occur after ingestion of a meal (e.g., a meal containing fats, starches or proteins). In this way, the release of medication 100 can be substantially synchronized or otherwise timed with the digestion of a meal. Such embodiments are particularly useful for the delivery of medication to control levels of blood glucose (e.g., insulin), serum cholesterol and serum triglycerides.

Various approaches are contemplated for biodegradation of release element 70. In particular embodiments, biodegradation of release element 70 from one or more conditions in the small intestine (or other location in the GI tract) can be achieved by one or more of the following: i) selection of the materials for the release element, ii) the amount of cross linking of those materials; and iii) the thickness and other dimensions of the release element. Lesser amounts of cross linking and or thinner dimensions can increase the rate of degradation and visa versa. Suitable materials for the release element can comprise biodegradable materials such as various enteric materials which are configured to degrade upon exposure to the higher pH in the intestines. Suitable enteric materials include, but are not limited to, the following: cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters as well as other enteric materials known in the art. The selected enteric materials can be copolymerized or otherwise combined with one or more other polymers to obtain a number of other particular material properties in addition to biodegradation. Such properties can include without limitation stiffness, strength, flexibility and hardness.

In alternative embodiments, the release element 70 can comprise a film or plug 70p that fits over or otherwise blocks guide tubes 30 and retains the tissue penetrating member 40 inside the guide tube. In these and related embodiments, tissue penetrating member 40 is coupled to a spring loaded actuating mechanism such that when the release element is degraded sufficiently, it releases the tissue penetrating member which then springs out of the guide tube to penetrate into the intestinal wall. In still other embodiments, release element 70 can be shaped to function as a latch which holds the tissue penetrating member 40 in place. In these and related embodiments, the release element can be located on the exterior or the interior of capsule 20. In the latter case, capsule 20 and/or guide tubes 30 can be configured to allow for the ingress of intestinal fluids into the capsule interior to allow for the degradation of the release element.

In some embodiments, actuating mechanism 60 can be actuated by means of a sensor 67, such as a pH sensor 68 or other chemical sensor which detects the presence of the capsule in the small intestine. Sensor 67 can then send a signal to actuating mechanism 60 or to an electronic controller 29c coupled to actuating mechanism 60 to actuate the mechanism. Embodiments of a pH sensor 68 can comprise an electrode-based sensor or it can be a mechanically-based sensor such as a polymer which shrinks or expands upon exposure to a selected pH or other chemical conditions in the small intestine. In related embodiments, an expandable/contractible sensor 67 can also comprise the actuating mechanism 60 itself by using the mechanical motion from the expansion or contraction of the sensor.

According to another embodiment for detecting that the device in the small intestine (or other location in the GI tract), sensor 67 can comprise pressure/force sensor such as strain gauge for detecting the number of peristaltic contractions that capsule 20 is being subject to within a particular location in the intestinal tract (in such embodiments capsule 20 is desirably sized to be gripped by the small intestine during a peristaltic contraction). Different locations within the GI tract have different number of peristaltic contractions. The small intestine has between 12 to 9 contractions per minute with the frequency decreasing down the length of the intestine. Thus, according to one or more embodiments, detection of the number of peristaltic contractions can be used to not only determine if capsule 20 is in the small intestine, but the relative location within the intestine as well. In use, these and related embodiments allow for release of medication 100 at a particular location in the small intestine.

As an alternative or supplement to internally activated drug delivery (e.g., using a release element and/or sensor), in some embodiments, the user may externally activate the actuating mechanism 60 to deliver medication 100 by means of RF, magnetic or other wireless signaling means known in the art. In these and related embodiments, the user can use a handheld communication device 13 (e.g., a hand held RF device such as a cell phone) as is shown in the embodiment of FIG. 1b, to send a receive signals 17 from device 10. In such embodiments, swallowable device may include a transmitter 28 such as an RF transceiver chip or other like communication device/circuitry. Handheld device 13 may not only includes signaling means, but also means for informing the user when device 10 is in the small intestine or other location in the GI tract. The later embodiment can be implemented through the use of logic resources 29 (e.g., a processor 29) coupled to transmitter 28 to signal to detect and singe to the user when the device is in the small intestine or other location (e.g., by signaling an input from the sensor). Logic resources 29 may include a controller 29c (either in hardware or software) to control one or more aspects of the process. The same handheld device can also be configured to alert the user when actuating mechanism 60 has been activated and the selected medication 100 delivered (e.g., using processor 29 and transmitter 28). In this way, the user is provided confirmation that medication 100 has been delivered. This allows the user to take other appropriate drugs/therapeutic agents as well as make other related decisions (e.g., for diabetics to eat a meal or not and what foods should be eaten). The handheld device can also be configured to send a signal to swallowable device 10 to override actuating mechanism 60 and so prevent delay or accelerate the delivery of medication 100. In use, such embodiments allow the user to intervene to prevent, delay or accelerate the delivery of medication, based upon other symptoms and/or patient actions (e.g., eating a meal, deciding to go to sleep, exercise etc). The user may also externally activate actuating mechanism 60 at a selected time period after swallowing the capsule. The time period can be correlated to a typical transit time or range of transit times for food moving through the user's GI tract to a particular location in the tract such as the small intestine.

Figure 10:
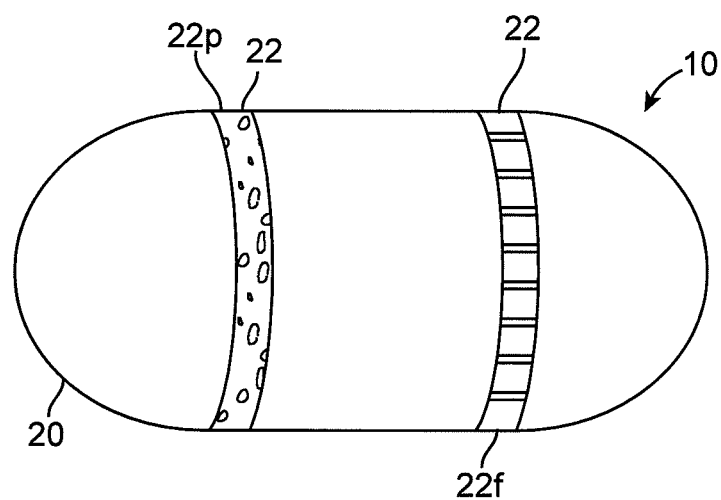
FIG. 10 shows an embodiment of a capsule having biodegradable seams including pores and/or perforations to accelerate biodegradation of the capsule.

In particular embodiments, the capsule 20 can include seams 22 of biodegradable material which controllably degrade to produce capsule pieces 23 of a selectable size and shape to facilitate passage through the GI tract as is shown in the embodiment of FIGS. 10a and 10b. Seams 22 can also include pores or other openings 22p for ingress of fluids into the seam to accelerate biodegradation as is shown in the embodiment of FIG. 10. Other means for accelerating biodegradation of seams 22 can include pre-stressing the seam and/or including perforations 22f in the seam as is also shown in the embodiment of FIG. 10. In still other embodiments, seam 22 can be constructed of materials and/or have a structure which is readily degraded by absorption of ultrasound energy, e.g. high frequency ultrasound (HIFU), allowing the capsule to be degraded into smaller pieces using externally or endoscopically (or other minimally invasive method) administered ultrasound.

Suitable materials for seams 22 can include one or more biodegradable materials described herein such as PGLA, glycolic acid etc. Seams 22 can be attached to capsule body 20 using various joining methods known in the polymer arts such as molding, hot melt junctions, etc. Additionally for embodiments of capsule 20 which are also fabricated from biodegradable materials, faster biodegradation of seam 22 can be achieved by one or more of the following: i) fabricating the seam from a faster biodegrading material, ii) pre-stressing the seam, or iii) perforating the seam. The concept of using biodegradable seams 22 to produce controlled degradation of a swallowable device in the GI tract can also be applied to other swallowable devices such as swallowable cameras (or other swallowable imaging device) to facilitate passage through the GI tract and reduce the likelihood of such a device becoming stuck in the GI tract. Accordingly, embodiments of biodegradable seam 22 can be adapted for swallowable imaging and other swallowable devices.

Figure 11:
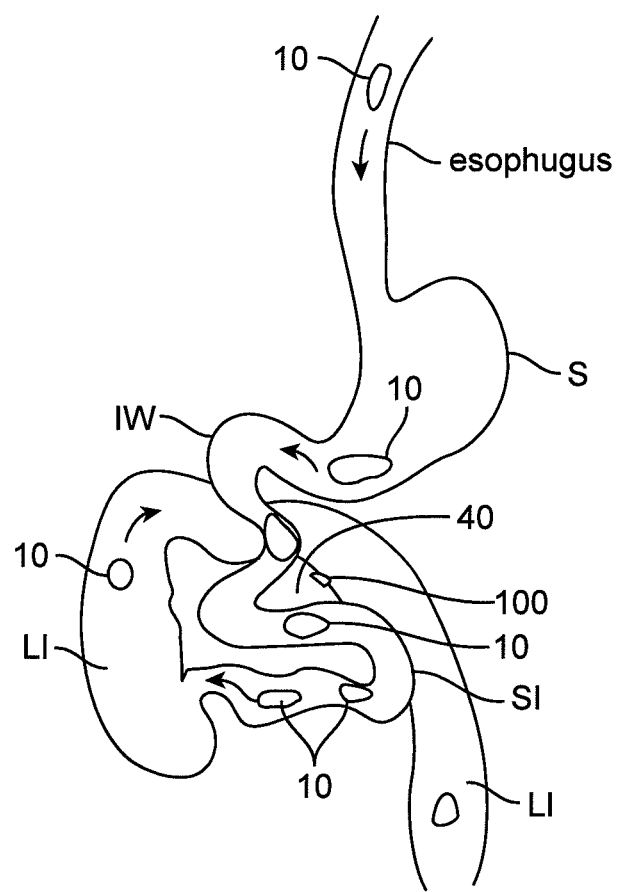
FIG. 11 is a lateral viewing illustrating use of an embodiment of a swallowable drug delivery device including transit of device in the GI tract and operation of the device to deliver drug.

Another aspect of the invention provides methods for the delivery of drugs and other therapeutic agents (in the form of medication 100) into the walls of the GI tract using one or more embodiments of swallowable drug delivery device 10. An exemplary embodiment of such a method will now be described. The described embodiment of drug delivery occurs in the small intestine SI. However, it should be appreciated that this is exemplary and that embodiments of the invention can be used for delivering drug in a number of locations in the GI tract including the stomach and the large intestine. For ease of discussion, the swallowable drug delivery device 10 will sometimes be referred to herein as a capsule. As described above, in various embodiments device 10 may be packaged as a kit 11 within sealed packaging 12 that includes device 10 and a set of instructions for use 15. If the patient is using a handheld device 13, the patient may instructed to enter data into device 13 either manually or via a bar code 18 (or other identifying indicia 18) located on the instructions 15 or packaging 12. If a bar code is used, the patient would scan the bar code using a bar code reader 19 on device 13. After opening packaging 12, reading the instructions 15 and entering any required data, the patient swallows an embodiment of the swallowable drug delivery device 10. Depending upon the drug, the patient may take the device 10 in conjunction with a meal (before, during or after) or a physiological measurement such as a blood glucose measurement. Capsule 20 is sized to pass through the GI tract and travels through the patient's stomach S and into the small intestine SI through peristaltic action as is shown in the embodiment of FIG. 11. Once in the small intestine, the release element 70 is degraded by the basic pH in the small intestine (or other chemical or physical condition unique to the small intestine) so as to actuate the actuating mechanism 60 and deliver medication 100 into the wall of the small intestine SI according to one or more embodiments of the invention. For embodiments including a hollow needle or other hollow tissue penetrating member 40, medication delivery is effectuated by using the actuating mechanism 60 to advance the needle 40 a selected distance into the mucosa of the intestinal wall IS, and then the medication is injected through the needle lumen 40 by advancement of the delivery member 50. The delivery member 50 is withdrawn and the needle 40 is then withdrawn back within the body of the capsule (e.g. by recoil of the spring) detaching from the intestinal wall. For embodiments of device 10 having multiple needles, a second or third needle 42, 43 can also be used to deliver additional doses of the same drug or separate drugs 101. Needle advancement can be done substantially simultaneously or in sequence. In preferred embodiments that use multiple needles, needle advancement can be done substantially simultaneously so as to anchor device 10 in the small intestine during drug delivery.

Figure 9A:
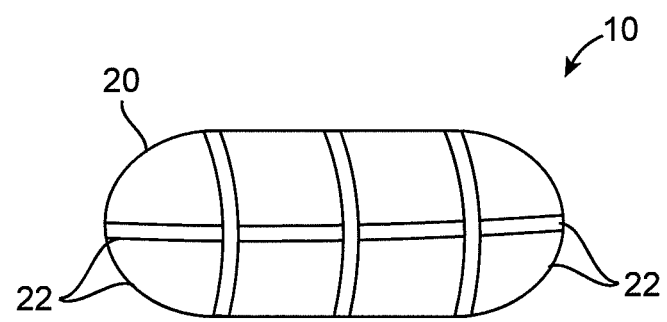
FIG. 9a shows an embodiment of a swallowable drug delivery device including a capsule having bio-degradable seams positioned to produce controlled degradation of the capsule in the GI tract.
Figure 9B:
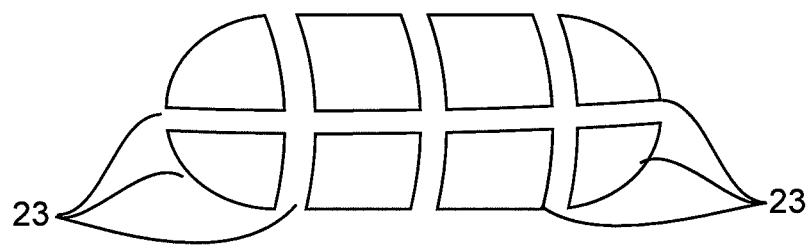
FIG. 9b shows the embodiment of FIG. 9a after having been degraded in the GI tract into smaller pieces.

After medication delivery, device 10 then passes through the intestinal tract including the large intestine LI and is ultimately excreted. For embodiments of the capsule 20 having biodegradable seams 22 or other biodegradable portions, the capsule is degraded in the intestinal tract into smaller pieces to facilitate passage through and excretion from the intestinal tract as is shown in the embodiments of FIGS. 9a and 9b. In particular embodiments having biodegradable tissue penetrating needles/members 40, should the needle get stuck in the intestinal wall, the needle biodegrades releasing the capsule 20 from the wall.

For embodiments of device 10 including a sensor 67, actuation of mechanism 60 can be effectuated by the senor sending a signal to actuating mechanism 60 and/or a processor 29/controller 29c coupled to the actuating mechanism. For embodiments of device 10 including external actuation capability, the user may externally activate actuating mechanism 60 at a selected time period after swallowing the capsule. The time period can be correlated to a typical transit time or range of transit times for food moving through the user's GI tract to a particular location in the tract such as the small intestine.

One or more embodiments of the above methods can be used for the delivery of preparations 100 containing therapeutically effective amounts of a variety of drugs and other therapeutic agents 101 to treat a variety of diseases and conditions. These include a number of large molecule peptides and proteins which would otherwise require injection due to chemical breakdown in the stomach, e.g., growth hormone, parathyroid hormone, insulin, interferons and other like compounds. Suitable drugs and other therapeutic agents which can be delivered by embodiments of the invention include various chemotherapeutic agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents (e.g., Furosimide), anti-migraine medication (sumatriptan), immune suppression agents (e.g., cyclosporine) and anti-parasitic agents such as various anti-malarial agents. The dosage of the particular drug can be titrated for the patient's weight, age or other parameter. Also the drug 101 to achieve a desired or therapeutic effect (e.g., insulin for blood glucose regulation, Furosimide for anti-seizure) can be less than the amount required should the drug have been delivered by conventional oral delivery (e.g., a swallowable pill that is digested in the stomach and absorbed through the wall of the small intestine). This is due to the fact that there is no degradation of the drug by acid and other digestive fluids in the stomach and the fact that all, as opposed to only a portion of the drug is delivered into the wall of the small intestine (or other lumen in the intestinal tract, e.g., large intestine, stomach, etc.). Depending upon the drug 101, the dose 102 delivered in preparation 100 can be in the range from 100 to 5% of a dose delivered by conventional oral delivery means to achieve a desired therapeutic effect (e.g., blood glucose regulation, seizure regulation, etc.) with even lower amounts contemplated. The particular dose reduction can be titrated based upon the particular drug, the condition to be treated, and the patient's weight, age and condition. For some drugs (with known levels of degradation in the intestinal tract) a standard dose reduction can be employed (e.g., 10 to 20%). Larger amounts of dose reduction can be used for drugs which are more prone to degradation and poor absorption. In this way, the potential toxicity and other side effects (e.g., gastric cramping, irritable bowel, hemorrhage, etc.) of a particular drug or drugs delivered by device 10 can be reduced because the ingested dose is lowered. This in turn, improves patient compliance because the patient has reduction both in the severity and incidence of side effects. Additional benefits of embodiments employing dose reduction of drug 101 include a reduced likelihood for the patient to develop a tolerance to the drug (requiring higher doses) and, in the case of antibiotics, for the patient to develop resistant strains of bacteria. Also, other levels of dose reduction can be achieved for patients undergoing gastric bypass operations and other procedures in which sections of the small intestine have been removed or its working (e.g., digestive) length effectively shortened.

In addition to delivery of a single drug, embodiments of swallowable drug delivery device 10 and methods of their use can be used to deliver a plurality of drugs for the treatment of multiple conditions or for the treatment of a particular condition (e.g., protease inhibitors for treatment HIV AIDS). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream, at about the same time. Due to difference in chemical makeup, molecular weight, etc, drugs can be absorbed through the intestinal wall at different rates, resulting in different pharmacokinetic distribution curves. Embodiments of the invention address this issue by injecting the desired drug mixtures at substantially the same time. This in turn, improves the pharmacokinetics and thus the efficacy of the selected mixture of drugs. Additionally, eliminating the need to take multiple drugs is particularly beneficial to patients who have one or more long term chronic conditions including those who have impaired cognitive or physical abilities.

In various applications, embodiments of the above methods can be used to deliver preparations 100 including drugs and therapeutic agents 101 to provide treatment for a number of medical conditions and diseases. The medical conditions and diseases which can be treated with embodiments of the invention can include without limitation: cancer, hormonal conditions (e.g., hypo/hyper thyroid, growth hormone conditions), osteoporosis, high blood pressure, elevated cholesterol and triglyceride, diabetes and other glucose regulation disorders, infection (local or septicemia), epilepsy and other seizure disorders, osteoporosis, coronary arrhythmia's (both atrial and ventricular), coronary ischemia anemia or other like condition. Still other conditions and diseases are also contemplated.

In many embodiments, the treatment of the particular disease or condition can be performed without the need for injecting the drug or other therapeutic agent (or other non-oral form of delivery such as suppositories) but instead, relying solely on the therapeutic agent(s) that is delivered into the wall of the small intestine or other portion of the GI tract. For example, diabetes or another glucose regulation disorder can be treated (e.g., by controlling blood glucose levels) solely through the use of insulin that is delivered into the wall of the small intestine without the need for the patient to ever inject insulin. Similarly, the patient need not take conventional oral forms of a drug or other therapeutic agent, but again rely solely on delivery into the wall of the small intestine using embodiments of the swallowable capsule. In other embodiments, the therapeutic agent(s) delivered into the wall of the small intestine can be delivered in conjunction with an injected dose of the agent(s). For example, the patient may take a daily dose of insulin or compound for blood glucose regulation using the embodiments of the swallowable capsule, but only need take an injected dose every several days or when the patient's condition requires it (e.g., hyperglycemia). The same is true for therapeutic agents that are traditionally delivered in oral form (e.g., the patient can take the swallowable capsule and take the conventional oral form of the agent as needed). The dosages delivered in such embodiments (e.g., the swallowed and injected dose) can be titrated as needed (e.g., using standard dose response curve and other pharmacokinetic methods can be used to determine the appropriate dosages). Also, for embodiments using therapeutic agents that can be delivered by conventional oral means, the dose delivered using embodiments of the swallowable capsule can be titrated below the dosage normally given for oral delivery of the agent since there is little or no degradation of the agent within the stomach or other portion of the intestinal tract (herein again standard dose response curve and other pharmacokinetic methods can be applied).

Various groups of embodiments of preparation 100 containing one or more drugs or other therapeutic agents 101 for the treatment of various diseases and conditions will now be described with references to dosages. It should be appreciated that these embodiments, including the particular therapeutic agents and the respective dosages are exemplary and the preparation 100 can comprise a number of other therapeutic agents described herein (as well as those known in the art) that are configured for delivery into a luminal wall in the intestinal tract (e.g., the small intestinal wall) using various embodiments of device 10. The dosages can be larger or smaller than those described and can be adjusted using one or more methods described herein or known in the art. In one group of embodiments, therapeutic agent preparation 100 can comprise a therapeutically effective dose of insulin for the treatment of diabetes and other glucose regulation disorders. The insulin can be human or synthetically derived as is known in the art. In one embodiment, preparation 100 can contain a therapeutically effective amount of insulin in the range of about 1-10 units (one unit being the biological equivalent of about 45.5 µg of pure crystalline insulin), with particular ranges of 2-4, 3-9, 4-9, 5-8 or 6-7. The amount of insulin in the preparation can be titrated based upon one or more of the following factors (herein, "glucose control titration factors"): i) the patient's condition (e.g., type 1 vs. type II diabetes; ii) the patients previous overall level of glycemic control; iii) the patient's weight; iv) the patient's age; v) the frequency of dosage (e.g., once vs. multiple times a day); vi) time of day (e.g., morning vs. evening); vii) particular meal (breakfast vs. dinner); vii) content/glycemic index of a particular meal (e.g., high fat/lipid and sugar content (e.g., foods causing a rapid rise in blood sugar) vs. low fat and sugar content; and viii) content of the patient's overall diet (e.g., amount of sugars and other carbohydrates, lipids and protein consumed daily).

In another group of embodiments, therapeutic agent preparation 100 can comprise a therapeutically effective dose of one or more incretins for the treatment of diabetes and other glucose regulation disorders. Such incretins can include Glucacon like peptides 1 (GLP-1) and their analogues, and Gastric inhibitory peptide (GIP). Suitable GLP-1 analogues include exenatide, liraglutide, albiglutide and taspoglutide as well as their analogues, derivatives and other functional equivalents. In one embodiment preparation 100 can contain a therapeutically effective amount of exenatide in the range of about 1-10 μg, with particular ranges of 2-4, 4-6, 4-8 and 8-10 μg respectively. In another embodiment, preparation 100 can contain a therapeutically effective amount of liraglutide in the range of about 1-2 mg (milligrams), with particular ranges of 1.0 to 1.4, 1.2 to 1.6 and 1.2 to 1.8 mg respectively. One or more of the glucose control titration factors can be applied to titrate the dose ranges for exenatide, liraglutide or other GLP-1 analogue or incretin.

In yet another group of embodiments, therapeutic agent preparation 100 can comprise a combination of therapeutic agents for the treatment of diabetes and other glucose regulation disorders. Embodiments of such a combination can include therapeutically effective doses of incretin and biguanide compounds. The incretin can comprise one or more GLP-1 analogues described herein, such as exenatide and the biguanide can comprise metformin (e.g., that available under the Trademark of GLUCOPHAGE® manufactured by Merck Santé S.A.S.) and its analogue, derivatives and other functional equivalents. In one embodiment, preparation 100 can comprise a combination of a therapeutically effective amount of exenatide in the range of about 1-10 μg and a therapeutically effective amount of metformin in a range of about 1 to 3 grams. Smaller and larger ranges are also contemplated with one or more of the glucose control titration factors used to titrate the respective dose of exenatide (or other incretin) and metformin or other biguanide. Additionally, the dosages of the exenatide or other incretin and metformin or other biguanide can be matched to improved level of glucose control for the patient (e.g., maintenance of blood glucose within normal physiological levels and/or a reduction in the incidence and severity of instances of hyperglycemia and/or hypoglycemia) for extended periods of time ranges from hours (e.g., 12) to a day to multiple days, with still longer periods contemplated. Matching of dosages can also be achieved by use of the glucose control regulation factors as well as monitoring of the patient's blood glucose for extended periods using glycosylated hemoglobin (known as hemoglobin A1c, HbA1c, A1C, or Hb1c) and other analytes and measurements correlative to long term average blood glucose levels.

In still yet another group of embodiments, therapeutic agent preparation 100 can comprise a therapeutically effective dose of growth hormone for the treatment of one or more growth disorders, as well as wound healing. In one embodiment, preparation 100 can contain a therapeutically effective amount of growth hormone in the range of about 0.1-4 mg, with particular ranges of 0.1-1, 1-4, 1-2 and 2-4, with still larger ranges contemplated. The particular dose can be titrated based on one or more of the following: i) the particular condition to be treated and its severity (e.g., stunted growth, vs. wound healing); ii) the patient's weight; iii) the patient's age; and iv) the frequency of dosage (e.g., daily vs. twice daily).

In still yet another group of embodiments, therapeutic agent preparation 100 can comprise a therapeutically effective dose of parathyroid hormone for the treatment osteoporosis or a thyroid disorder. In one embodiment, preparation 100 can contain a therapeutically effective amount of parathyroid hormone in the range of about 1-40 μg, with particular ranges of 10-20, 20-30, 30-40 and 10-40 μg, with still larger ranges contemplated. The particular dose can be titrated based on one or more of the following: i) the particular condition to be treated and its severity (e.g., the degree of osteoporosis as determined by bone density measurements); ii) the patient's weight; iii) the patient's age; and iv) the frequency of dosage (e.g., daily vs. twice daily).

Drug delivery compositions and components of known drug delivery systems may be employed and/or modified for use in some embodiments of the inventions described herein. For example, microneedles and other microstructures used for delivery of drugs through the skin surface with drug patches may be modified and included within the capsules described herein and used to instead deliver a drug into a lumen wall of the gastrointestinal tract. Suitable polymer microneedle structures may be commercially available from Corium of California, such as the MicroCor™ micro delivery system technology. Other components of the MicroCor™ patch delivery systems, including drug formulations or components, may also be incorporated into the capsules described herein. Alternatively, a variety of providers are commercially available to formulate combinations of polymers or other drug-delivery matricees with selected drugs and other drug preparation components so as to produce desired shapes (such as the releasable tissue-penetrating shapes described herein) having desiragle drug release characteristics. Such providers may, for example, include Corium, SurModics of Minnesota, BioSensors International of Singapore, or the like.

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device can be sized and otherwise adapted for various pediatric and neonatal applications as well as various veterinary applications. Also those skilled in the art will recognize, or be able to ascertain using no more than routine experimentation, numerous equivalents to the specific devices and methods described herein. Such equivalents are considered to be within the scope of the present invention and are covered by the appended claims below.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A therapeutic agent preparation for delivery into a lumen of the intestinal tract, the lumen having a lumen wall, the preparation comprising a therapeutically effective dose of at least one therapeutic agent, wherein the preparation is a solid shaped as a tissue penetrating member having a dart-like structure, the tissue penetrating member configured to be contained in an oval shaped swallowable capsule and to be delivered from the capsule to penetrate and be advanced into the lumen wall by the application of force on the tissue penetrating member, wherein the solid degrades within the lumen wall to release the dose of therapeutic agent.

2. The preparation of claim 1, wherein the lumen is the small intestine and the preparation is configured to degrade within the wall of the small intestine.

3. The preparation of claim 1, wherein the preparation comprises at least one pharmaceutical excipient.

4. The preparation of claim 1, wherein the preparation is configured to have a selectable surface area to volume ratio to achieve a selectable rate of release of the therapeutic agent in the lumen wall.

5. The preparation of claim 1, wherein an amount of the therapeutic agent within the preparation to produce a desired therapeutic effect is less than an amount to produce a corresponding effect if the agent was orally delivered without enclosure in the swallowable capsule.

6. The preparation of claim 1, wherein the preparation is configured to be coupled to an actuator having a first configuration and a second configuration, the preparation being contained within the capsule in the first configuration and advanced out of the capsule and into the lumen wall in the second configuration.

7. The preparation of claim 1, wherein the preparation is configured to be delivered within a lumen of a tissue penetrating member.

8. The preparation of claim 1, wherein the therapeutic agent comprises a therapeutically effective dose of an incretin for the treatment of diabetes or a glucose regulation disorder.

9. The preparation of claim 8, wherein the incretin comprises a glucagon like peptide-1 (GLP-1), a GLP-1 analogue, exenatide, liraglutide, albiglutide, taspoglutide or a gastric inhibitory polypeptide (GIP).

10. The preparation of claim 8, wherein the incretin comprises exenatide and the dose is in a range from about 1 to 10 µg.

11. The preparation of claim 8, wherein the incretin comprises liraglutide and the dose is in a range from about 1 to 2 mg.

12. The preparation of claim 1, wherein the therapeutic agent comprises a combination of therapeutic agents for the treatment of diabetes or a glucose regulation disorder.

13. The preparation of claim 12, wherein the combination comprises a therapeutically effective dose of an incretin and a therapeutically effective dose of a biguanide.

14. The preparation of claim 13, wherein the incretin comprises exenatide and the biguanide comprises metformin.

15. The preparation of claim 13, wherein the dosages of the incretin and the biguanide are matched to produce an improved level of blood glucose control for an extended period.

* * * * *